(12) United States Patent
Dellacqua et al.

(10) Patent No.: US 11,173,090 B2
(45) Date of Patent: Nov. 16, 2021

(54) NERVE DE-TENSIONING METHOD AND APPARATUS

(71) Applicant: Burwood, LLC, Carmel, IN (US)

(72) Inventors: Dale Dellacqua, Bloomington, IN (US); Michael Broderick, Zionsville, IN (US); Souheil F. Haddad, Bloomington, IN (US)

(*) Notice: Subject to any disclaimer, the term of this patent is extended or adjusted under 35 U.S.C. 154(b) by 757 days.

(21) Appl. No.: 15/179,600

(22) Filed: Jun. 10, 2016

(65) Prior Publication Data

US 2017/0095373 A1    Apr. 6, 2017

Related U.S. Application Data

(60) Provisional application No. 62/173,785, filed on Jun. 10, 2015.

(51) Int. Cl.
*A61H 1/02* (2006.01)
*A61F 13/08* (2006.01)
*A61F 5/02* (2006.01)

(52) U.S. Cl.
CPC ............. *A61H 1/0237* (2013.01); *A61F 5/02* (2013.01); *A61F 13/08* (2013.01)

(58) Field of Classification Search
CPC ...... A61H 1/02; A61H 1/0244; A61H 1/0266; A61H 1/0237–0266; A61H 3/00; A61H 3/08; A61H 2003/007; A61H 1/0255–0266; A61F 5/02; A61F 5/04–048; A61F 5/37; A61F 5/3715; A61F 13/06–062; A61F 13/064–085; A61F 5/042; A61F 13/08; A61F 13/085; A61F 13/0855; A41D 13/00–0007; A41D 13/0015; A41D 2400/38; A41D 13/0007; A63B 21/00–00043; A63B 21/00058; A63B 21/00069; A63B 21/00185; A63B 21/065; A63B 69/0022–0035

See application file for complete search history.

(56) References Cited

U.S. PATENT DOCUMENTS

| | | | | | |
|---|---|---|---|---|---|
| 4,216,547 | A | * | 8/1980 | Picchione | A41D 13/0543 2/22 |
| 4,910,802 | A | * | 3/1990 | Malloy | A41D 13/0015 2/227 |
| 2012/0270708 | A1 | * | 10/2012 | Paulos | A61F 5/0102 482/124 |
| 2015/0202512 | A1 | * | 7/2015 | Antoine | A63B 21/4015 482/131 |

FOREIGN PATENT DOCUMENTS

FR    2986402 A1 *  8/2013  ............. A41D 13/00

* cited by examiner

*Primary Examiner* — Michelle J Lee
(74) *Attorney, Agent, or Firm* — Brennan, Manna & Diamond, LLC

(57) ABSTRACT

A method and apparatus to de-tension or unload the sciatic or other major nerve or muscle group compressing a nerve of a user.

9 Claims, 10 Drawing Sheets

NERVE DE-TENSIONING METHOD AND APPARATUS

This application claims priority under 35 U.S.C. § 119 to U.S. Provisional Application No. 62/173,785, entitled Nerve De-Tensioning Method and Apparatus which was filed on Jun. 10, 2015, and is herein incorporated by reference in its entirety.

A method and apparatus for de-tensioning a nerve, in an exemplary embodiment the sciatic nerve of the leg is disclosed although the teachings may be applied to de-tensioning other nerves of the legs and arms. The sciatic nerve is a large nerve that innervates nearly the entire lower leg of humans. It is formed from the L4 to S3 segments emerging from the lower back through the buttock and down each leg. When the nerve is injured or irritated it can cause pain. Often the pain is difficult to control and surgical decompression may be necessary.

BRIEF DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

FIG. 1 is front perspective view of a de-tensioning apparatus.

FIG. 2 is rear perspective view of the de-tensioning apparatus of FIG. 1.

FIG. 3 is front elevation view of the de-tensioning apparatus of FIG. 1.

FIG. 4 is rear elevation view of the de-tensioning apparatus of FIG. 1.

FIG. 5 is right side view of the de-tensioning apparatus of FIG. 1.

FIG. 6 is front perspective view of an alternate embodiment of a de-tensioning apparatus.

FIG. 7 is front elevation view of an alternate embodiment of a de-tensioning apparatus.

FIG. 8 is rear elevation view of the de-tensioning apparatus of FIG. 7.

FIG. 9 is front elevation view of an alternate embodiment of a de-tensioning apparatus.

FIG. 10 is rear elevation view of the de-tensioning apparatus of FIG. 9.

DETAILED DESCRIPTION

Generally speaking, a system and method as used herein includes but is not limited to an apparatus urging at least one leg of a user to an unextended or minimized extension state. In one embodiment, the apparatus includes a compression-type hose or garment covering the lower body portion of a user, in one instance from about the waist down. The apparatus also may include an integrated foot stirrup or sock, a lower-back support, and an elastic band or bands in channels guiding the band or bands to preferred anatomical locations on the user. In one embodiment, the elastic band or bands travel through channels adjacent to posterior ankle, posterior knee, anterior hip and/or circumferential waist to provide continuous dynamic flexion to the hip, knee and foot to minimize against leg and/or foot extensions that increase tension on the sciatic nerve. The resulting flex of hip, knee and/or ankle reduce leg extension and de-tension the sciatic nerve while a user is awake or asleep alleviating or reducing pain associated with sciatic nerve injury or irritation, as well as reducing the weight of the extremity through supporting bands proximal to the affected limb.

With reference to FIGS. 1-6, an exemplary device 100 is shown. In an embodiment, the device includes a close fitting garment 110, akin to compression shorts or pants. The garment 110 includes waist guides or channels 114 at or near a waistband 118. While illustrated with two front waist channels 114 and two back waist channels 116, it is appreciated that the waistband 118 itself may function as a single waist channel surrounding a top periphery or disposed on a proximal side of the garment 110. The garment 110 may also include medial and lateral knee guides or channels 120, 122 and medial and lateral ankle guides or channels 130, 132. The garment 110 may include an integrated or separate foot stirrup 140 or sock 142 (FIG. 6) disposed on a distal side of the garment 110, where the stirrup 140 or sock 142 may include medial and lateral ankle guides, channels or an adjustable termination point 150 toward a distal end for elastic band or bands as will be further discussed below.

Device 100 may further include an elastic band or bands 160 arranged to de-tension a nerve or muscle group in the leg or arm or any nerve crossing a joint, in this embodiment by encouraging the leg to a flexed posture. Band 160 may be connected to or adjustably connected to a lateral lower or distally located end 166 of garment 110 and/or, in an embodiment not illustrated, on a lateral side of foot stirrup or sock 140. Band 160 may be passed through the lateral ankle guide 132 and lateral knee guide 122. Band 160 may then be passed through back waist channels 116 and around through front waist channels 114 and back down a medial side. On the medial return, band 160 may be passed through medial knee guide 120, medial ankle guide 130 and connected to or user adjustably connected to a medial lower end 168 of garment 110 and/or, in an embodiment not illustrated, on a medial side of foot stirrup or sock 140. The device may include an elastic band similarly arranged on the other leg of garment 110. Band or bands 160 may pass through discrete channels as described or through continuous or nearly continuous channels on or associated with garment 110. Additionally, the channels may be disposed on an interior side of garment or on an exterior side as illustrated.

With reference now to FIGS. 7 and 8, an alternate embodiment of a de-tensioning device 700 is shown. Device 700 may include a waist belt 704 connected to or adjustably connected to at least one elastic band, 710. While the waist belt 704 and elastic band 710 are shown as being worn over and above undergarment 716, they need not be. Indeed, waist belt 704 and elastic band 710 may themselves be formed as part of an undergarment. The device 700 may further include an over the knee sock 718 fitted with a medial knee guide 720 and lateral knee guide 722 to accommodate and position elastic band 710. The over the knee sock 718 may also be fitted with a medial ankle guide 730 and lateral ankle guide 732 to accommodate and position elastic band 710. In embodiments, medial ankle guide 730 and lateral ankle guide 732 may additionally function as an adjustable termination for elastic band 710. In use, elastic bands 710 are tightened as desired by a user and device 700 encourages a flex in the leg of the user de-tensioning at least the sciatic nerve. We have identified the posterior ankle, posterior knee, anterior hip and/or circumferential waist as areas to provide tension resulting in flex of hip, knee and/or ankle reducing leg extension, de-tensioning the sciatic nerve and alleviating or reducing pain associated with sciatic nerve injury or irritation while a user is awake or asleep.

Figure 1:
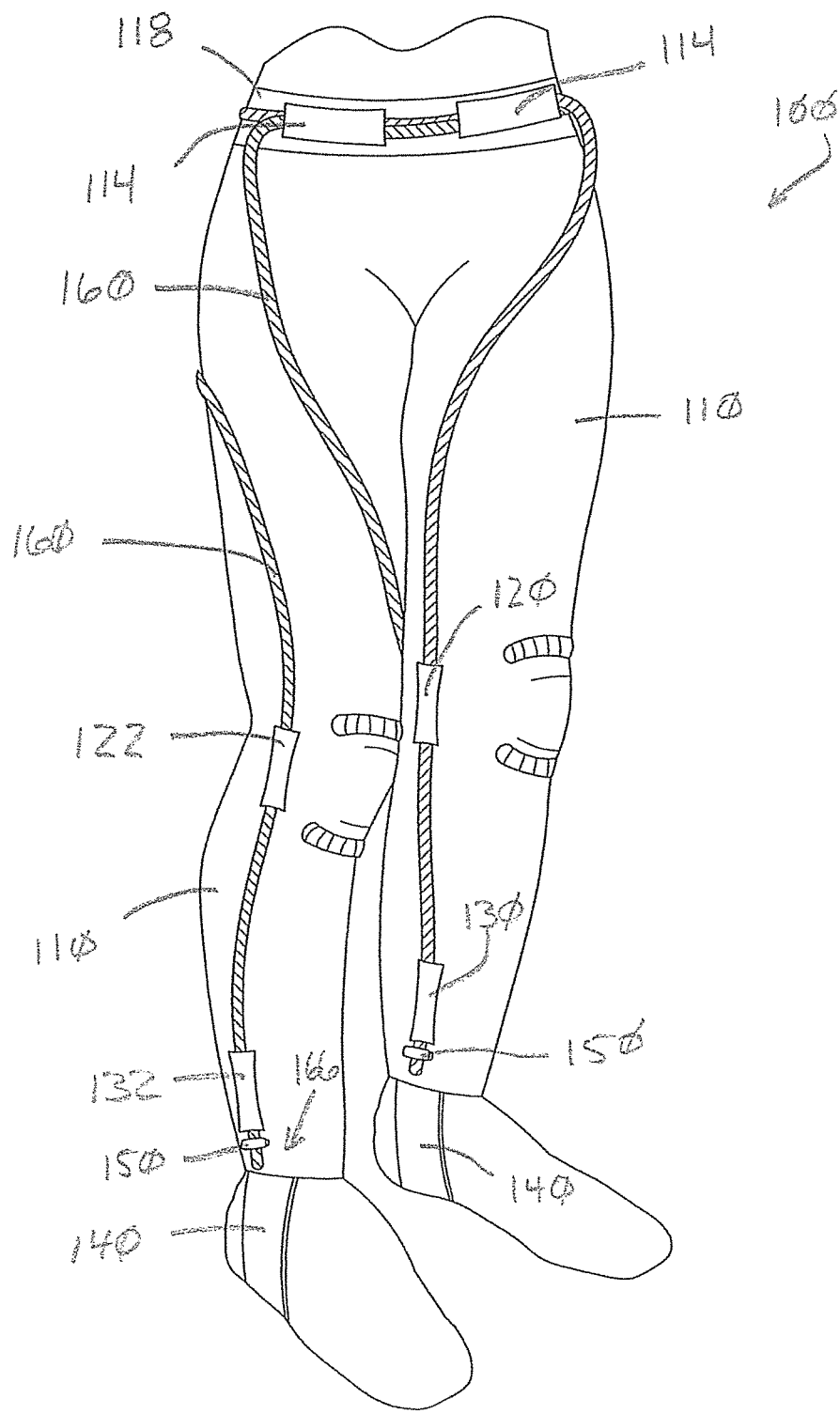
Figure 2:
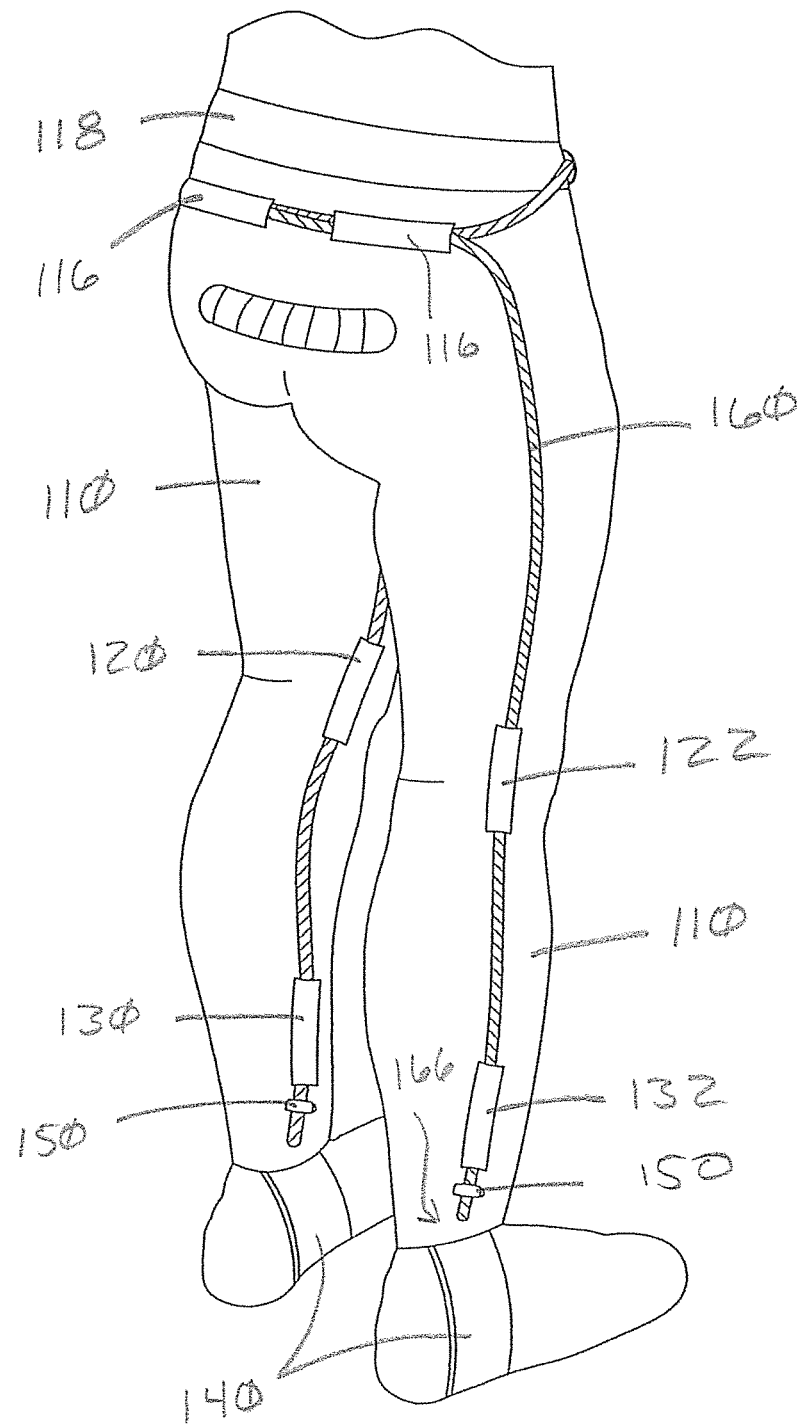
Figure 3:
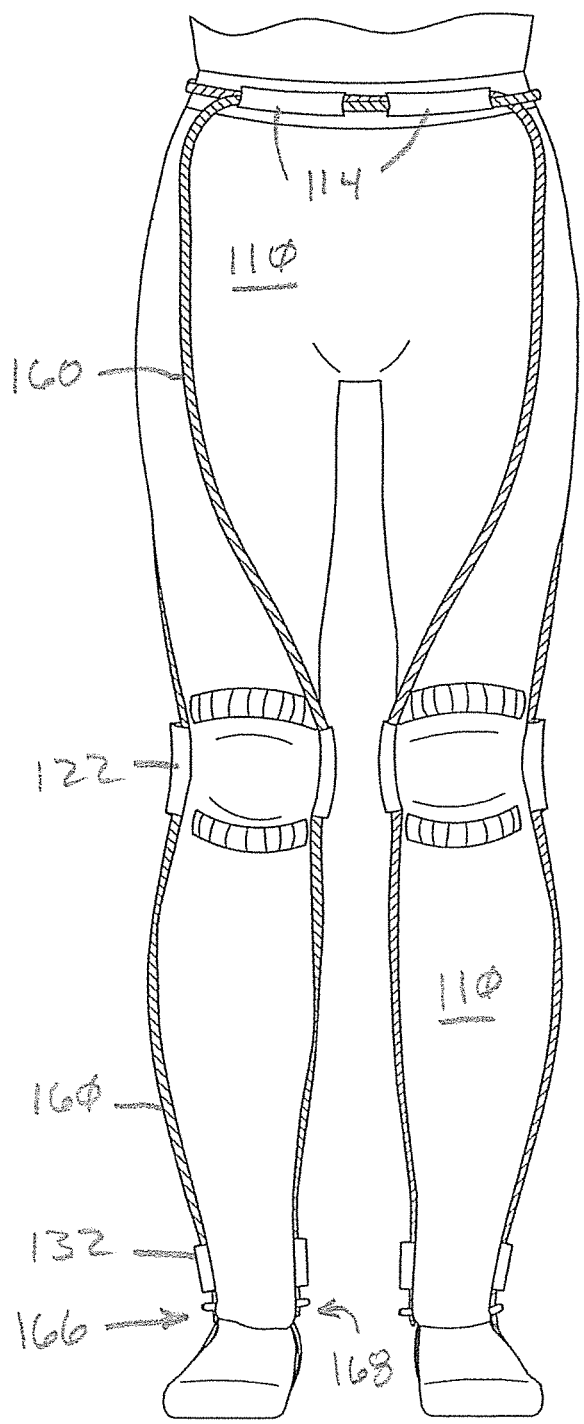
Figure 4:
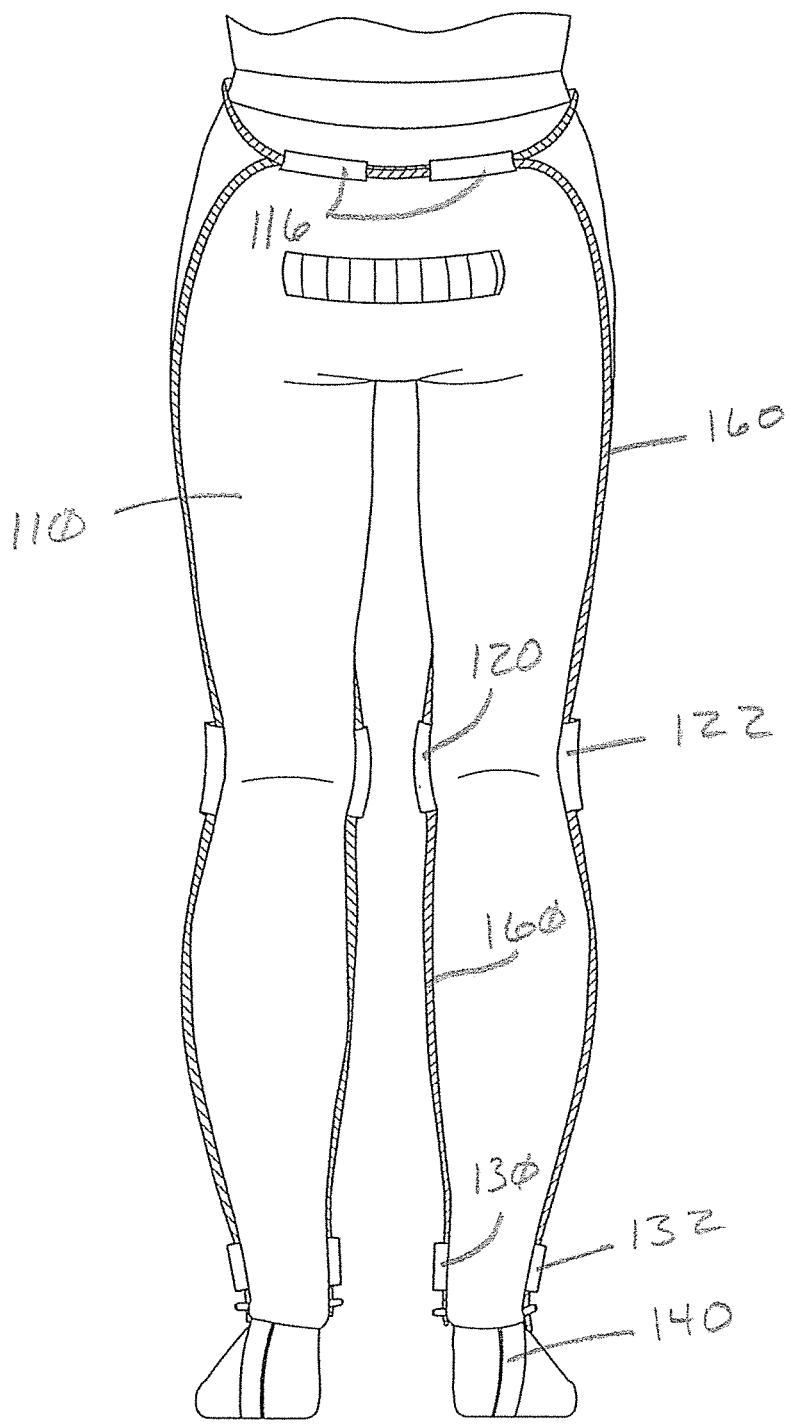
Figure 5:
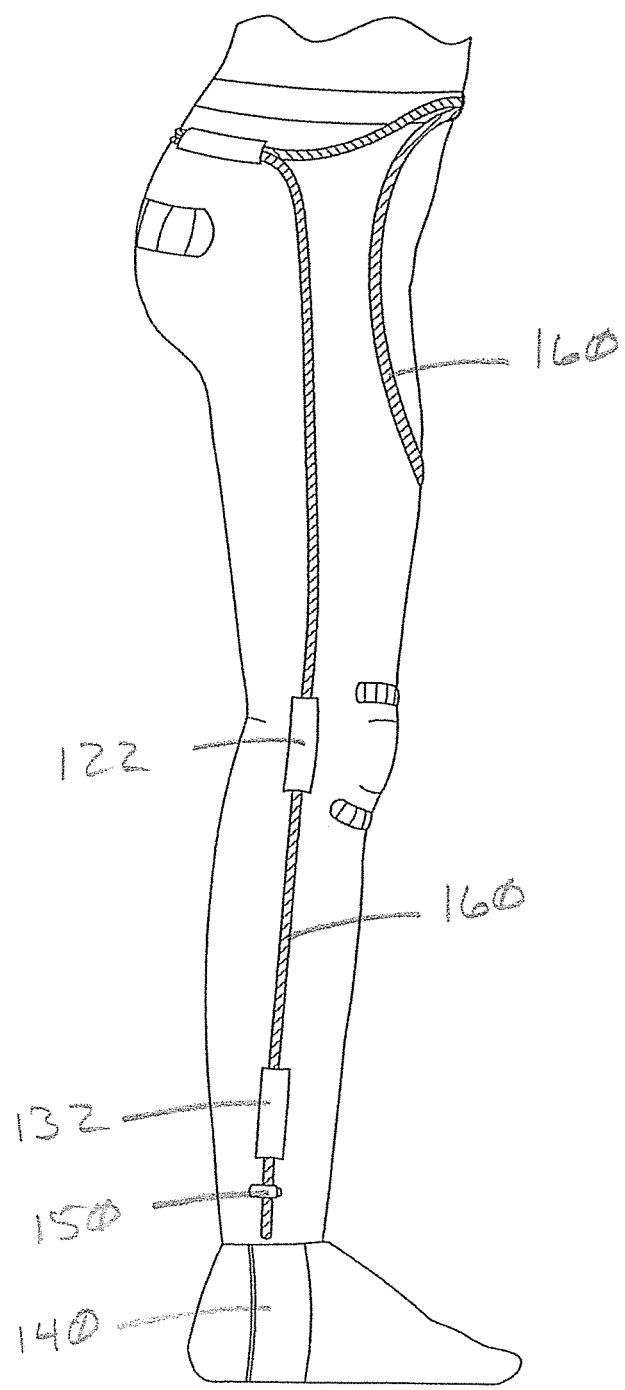
Figure 6:
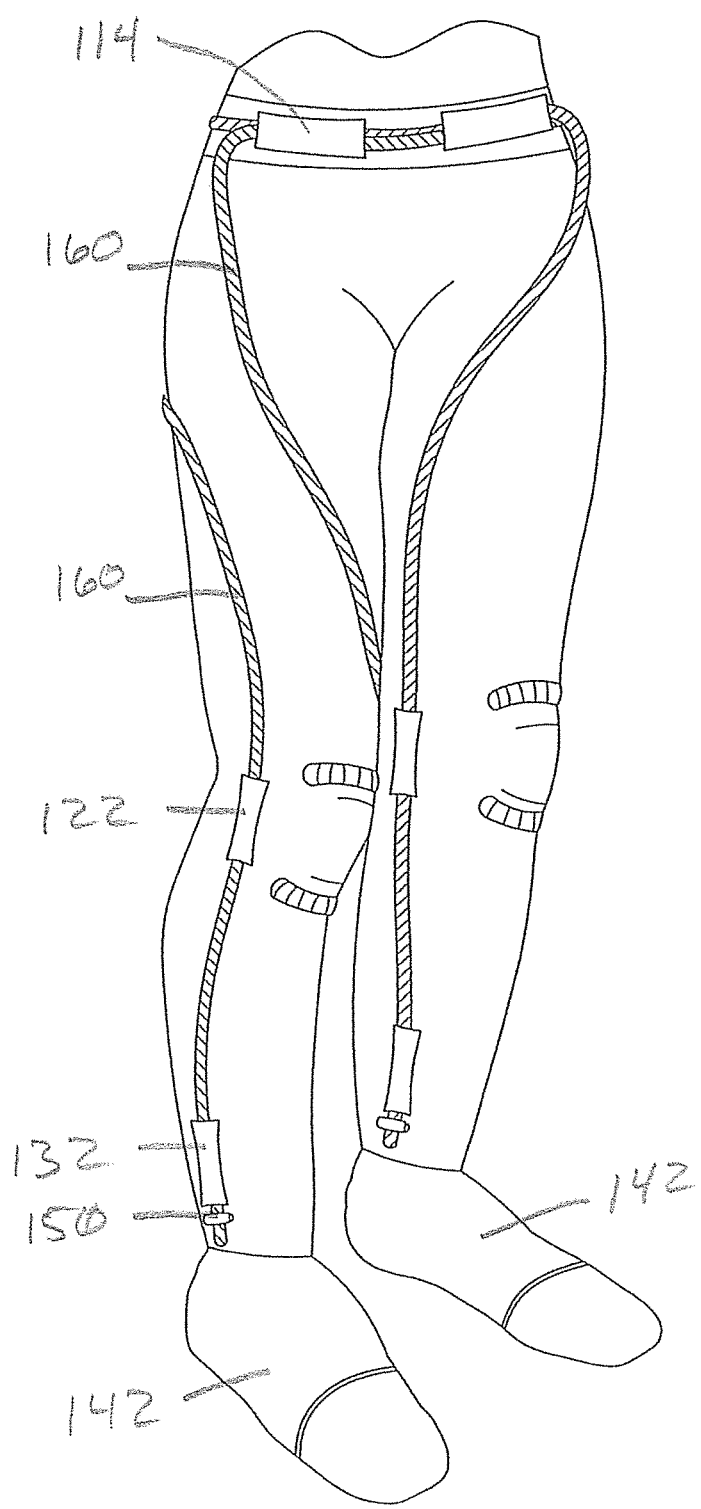
Figure 7:
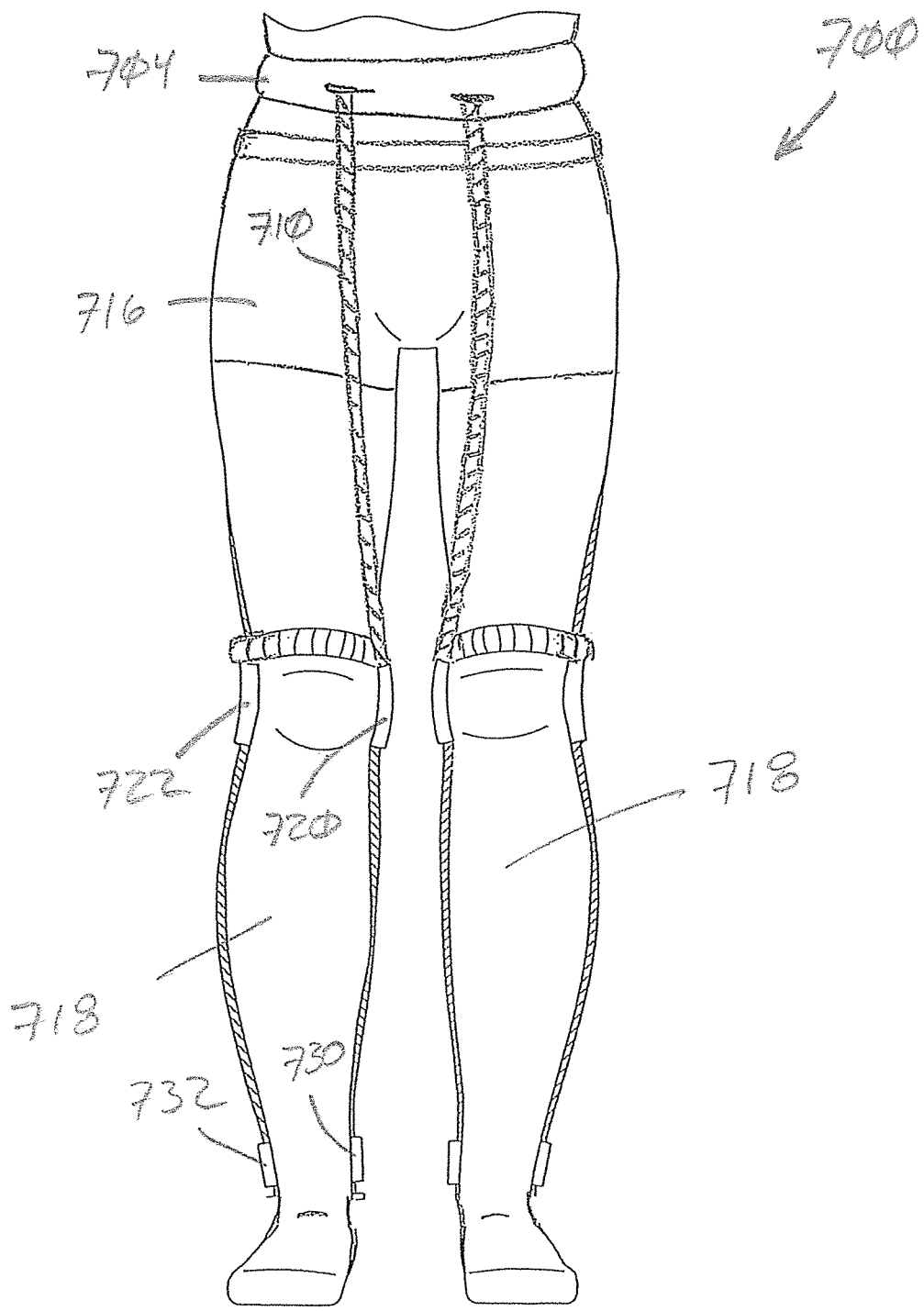
Figure 8:
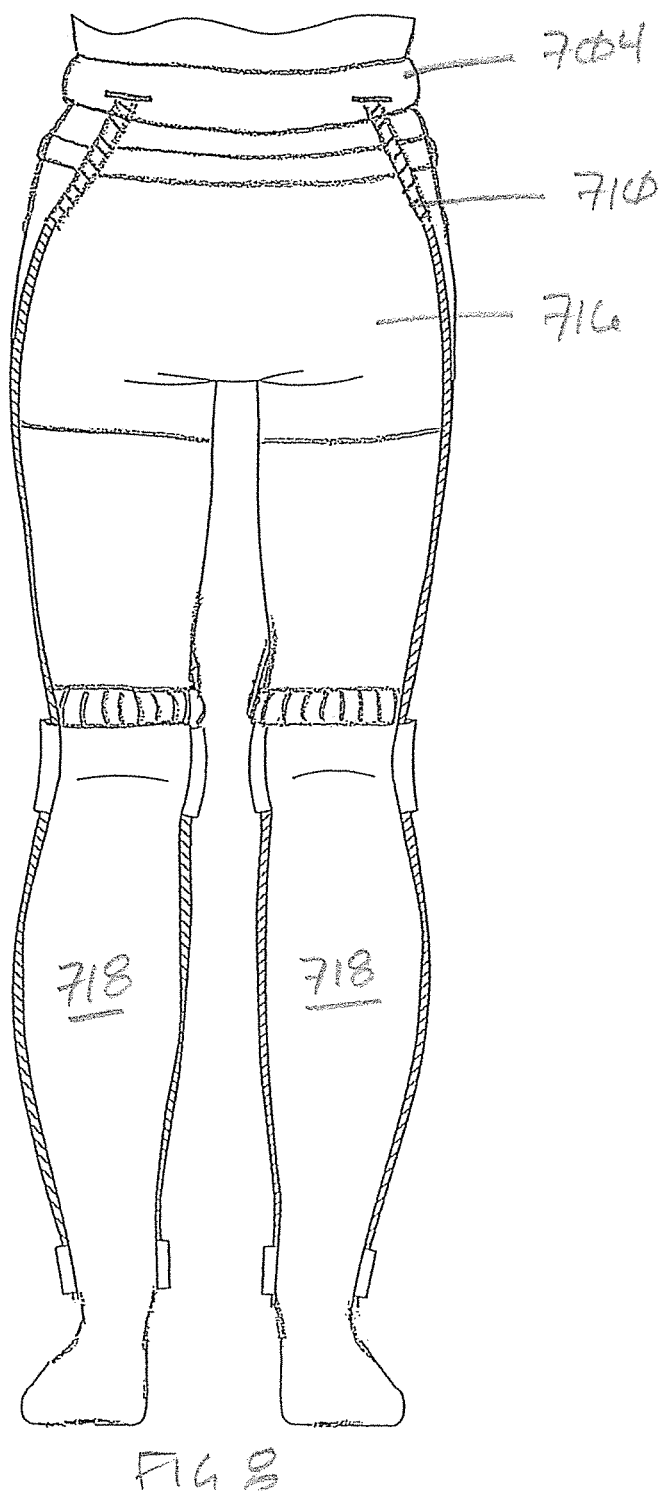
Figure 9:
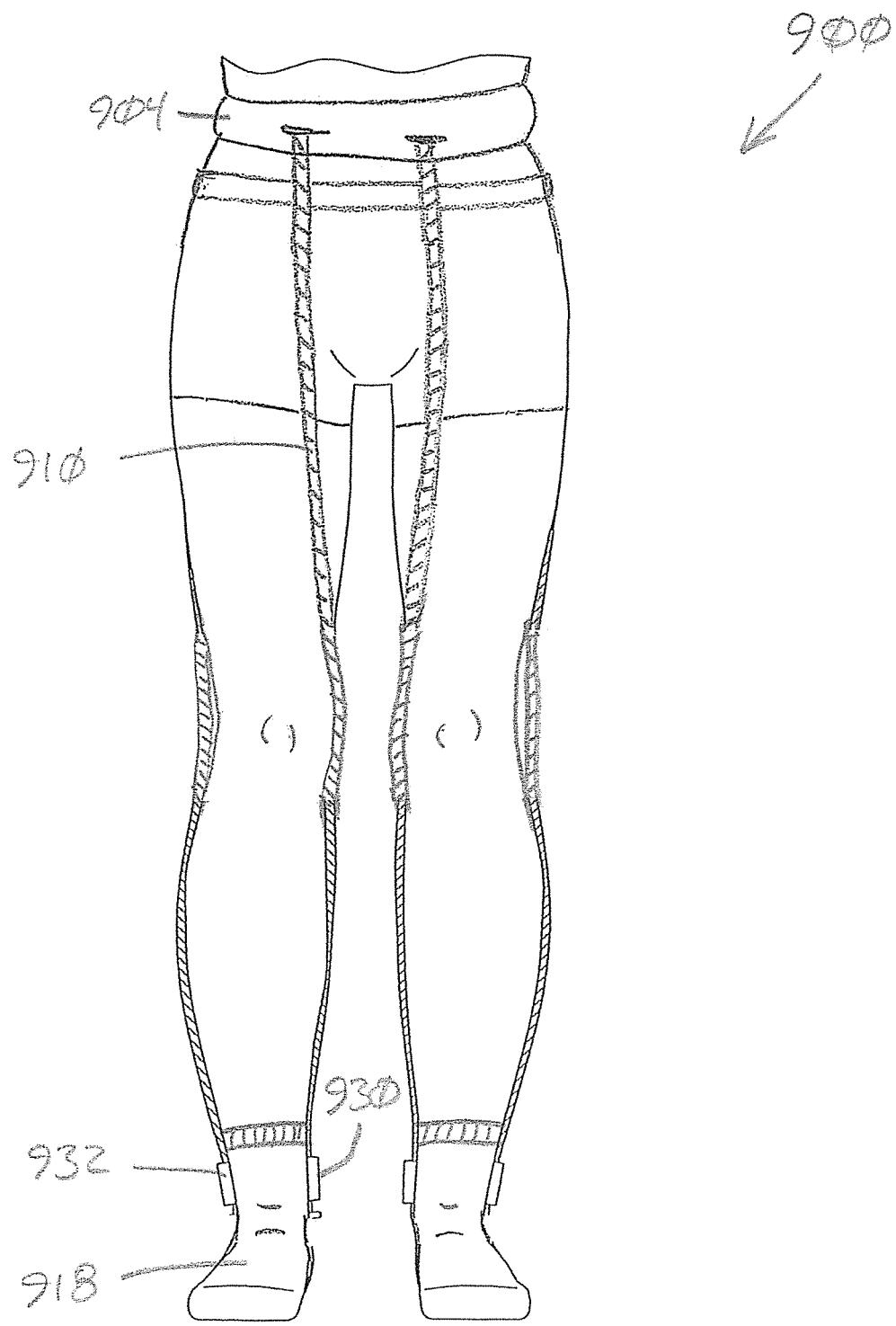
Figure 18D:
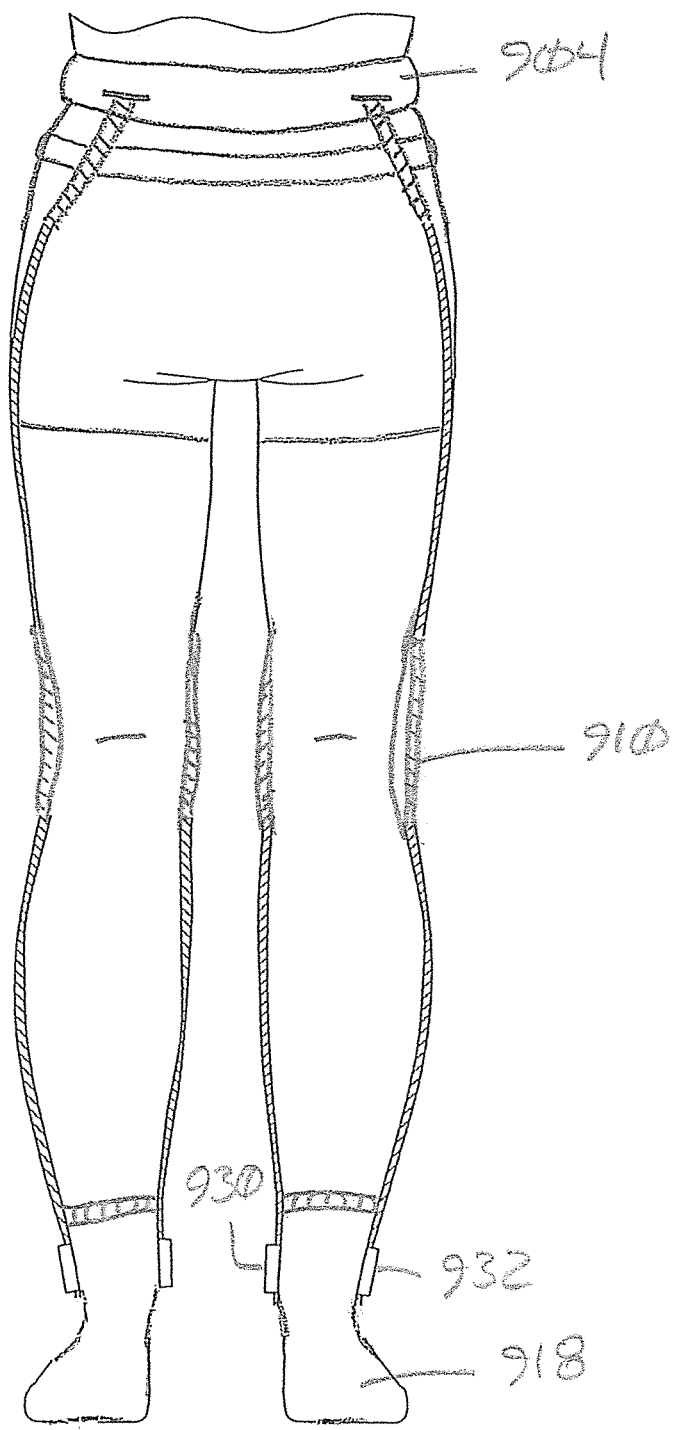

With reference to FIGS. 9 and 10, an alternate embodiment of a de-tensioning device 900 is shown. Device 900 may include a waist belt 904 connected to or adjustably connected to at least one elastic band 910. The device 900 may further include an ankle sock 918 fitted with a medial ankle guide 930 and lateral ankle guide 932 to accommodate and position elastic band 910. Medial ankle guide 930 and lateral ankle guide 932 may additionally function as an adjustable termination for elastic band 910. In use, elastic bands 910 are tightened as desired by a user and device 900 encourages a flex in the leg of the user de-tensioning at least the sciatic nerve. We have identified the posterior ankle, posterior knee, anterior hip and/or circumferential waist as areas to provide tension resulting in flex of hip, knee and/or ankle reducing leg extension, de-tensioning the sciatic nerve and alleviating or reducing pain associated with sciatic nerve injury or irritation while a user is awake or asleep.

As used herein, "connection," "connected" or "connectable" means both directly, that is, without other intervening elements or components, and indirectly, that is, with another component or components arranged between the items identified or described as being connected. To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Similarly, when the applicants intend to indicate "one and only one" of A, B or C, the applicants will employ the phrase "one and only one." Thus, use of the term "or" herein is the inclusive, and not the exclusive use. See, Bryan A. Garner, A Dictionary of Modern Legal Usage 624 (2d. Ed. 1995).

What is claimed is:

1. An apparatus comprising:
a compression garment to be worn by a user desiring to reduce leg extension and de-tension a nerve, the garment having a waist and a first and second legs depending therefrom and sized to at least partially cover at least one leg of the user wearing the garment;
a first channel comprising a pair of front waist guides and a pair of back waist guides disposed on the waist of the compression garment and corresponding to a waist of the user when wearing the garment;
a second channel disposed along the first leg of the garment and corresponding to a location outside and behind a knee of a first leg of the user when wearing the garment;
a third channel disposed along the first leg of the garment at a distal end of the compression garment and corresponding to a location outside an ankle of the user when wearing the garment;
a fourth channel disposed along the first leg of the garment and corresponding to a location inside and behind the knee of the user when wearing the garment;
a fifth channel disposed along the first leg of the garment at the distal end of the compression garment and corresponding to a location inside the ankle of the user when wearing the garment; and
an elastic band terminating at the distal end of the compression garment adjacent to the fifth channel and extending proximally therefrom through the fifth channel to the fourth channel and then to the first channel through the pair of front waist guides, then through the pair of back waist guides to extend partially around the waist of the user and extending therefrom distally through the second channel to the third channel and terminating at the distal end of the compression garment adjacent to the third channel at an adjustable termination point.

2. The apparatus as set forth in claim 1, the elastic band terminating at the distal end of the compression garment adjacent to the fifth channel at a second adjustable termination point.

3. The apparatus as set forth in claim 2, wherein the adjustable termination point is configured to be positioned along the first leg of the user and the second adjustable termination point is configured to be positioned along the first leg of the user.

4. The apparatus as set forth in claim 1, wherein tension in the elastic band is user adjustable at the distal end of the compression garment adjacent to the third channel.

5. The apparatus as set forth in claim 1, further comprising a foot stirrup or sock at the distal end of the compression garment wherein tension in the elastic band is user adjustable adjacent to the foot stirrup or sock.

6. The apparatus as set forth in claim 1, where the elastic band extends directly from the second channel to the third channel.

7. The apparatus as set forth in claim 1, where the elastic band extends directly from the fourth channel to the fifth channel.

8. The apparatus as set forth in claim 1, wherein the elastic band does not extend over a shoulder of the user.

9. The apparatus as set forth in claim 1, wherein the elastic band is configured to wrap around the waist of the user.

* * * * *